United States Patent
Sun et al.

(10) Patent No.: US 10,398,696 B2
(45) Date of Patent: Sep. 3, 2019

(54) COMBINATIONS FOR TREATMENT OF CANCER

(71) Applicant: Stichting Het Nederlands Kanker Instituut-Antoni van Leeuwenhoek Ziekenhuis, Amsterdam (NL)

(72) Inventors: Chong Sun, Amsterdam (NL); Rene Bernards, Amsterdam (NL)

(73) Assignee: STICHTING HET NEDERLANDS KANKER INSTITUUT-ANTONI VAN LEEUWENHOEK ZIEKENHUIS, Amsterdam (NL)

( * ) Notice: Subject to any disclaimer, the term of this patent is extended or adjusted under 35 U.S.C. 154(b) by 9 days.

(21) Appl. No.: 14/775,009

(22) PCT Filed: Mar. 12, 2014

(86) PCT No.: PCT/NL2014/050148
§ 371 (c)(1),
(2) Date: Sep. 11, 2015

(87) PCT Pub. No.: WO2014/142660
PCT Pub. Date: Sep. 18, 2014

(65) Prior Publication Data
US 2016/0022680 A1    Jan. 28, 2016

(30) Foreign Application Priority Data
Mar. 12, 2013 (NL) ..................................... 2010440

(51) Int. Cl.
*A61K 31/517* (2006.01)
*A61K 45/06* (2006.01)
*A61K 31/4184* (2006.01)
*A61K 31/5377* (2006.01)
*A61K 31/166* (2006.01)

(52) U.S. Cl.
CPC .......... *A61K 31/517* (2013.01); *A61K 31/166* (2013.01); *A61K 31/4184* (2013.01); *A61K 31/5377* (2013.01); *A61K 45/06* (2013.01)

(58) Field of Classification Search
CPC ................ A61K 31/517; A61K 31/166; A61K 31/4184; A61K 31/5377; A61K 45/06
See application file for complete search history.

(56) References Cited

PUBLICATIONS

Walters et al (Neoplasia, vol. 15 No. 2 Feb. 2013 pp. 143-155).*
Ramalingan et al (Journal of Clinical Oncology, vol. 30 No. 27 Sep. 20, 2012).*
Adjei et al (J Thorac Oncol. 2008;3: Suppl 2, S160-S163).*
"Dacomitinib Plus PD-0325901 in Advanced KRAS Mutant Malignancies (MI3DAP)" ClinicalTrials.gov, (Jan. 2014).
(Continued)

*Primary Examiner* — Angela C Brown-Pettigrew
(74) *Attorney, Agent, or Firm* — Browdy and Neimark, PLLC

(57) ABSTRACT

The current disclosure relates to pharmaceutical combinations and compositions useful in the treatment of certain types of cancer. The disclosure also relates to method of treatment these certain types of cancer. In particular, the disclosure relates to the combined use of inhibitors of MEK, EGFR and ERBB2 in the treatment of KRAS-mutant lung cancer, and KRAS-mutant colon cancer.

5 Claims, 3 Drawing Sheets

(56) References Cited

PUBLICATIONS

Walters Dustin M et al., "Inhibition of the Growth of Patient-Derived Pancreatic Cancer Xenografts with the MEK Inhibitor Trametinib Is Augmented by Combined Treatment with the Epidermal Growth Factor Receptor/HER2 Inhibitor Lapatinib" Neoplasia. Neoplasia Press, pp. 143-155, vol. 15. No. 2 (Feb. 2013).

Huang Ming-Hung et al.,"MEK inhibitors reverse resistance in epidermal growth factor receptor mutation lung cancer cells with acquired resistance to gefitinib" Molecular Oncology, pp. 112-120, vol. 7. No. 1 (Feb. 2013).

Adi F Gazdar, "Epidermal growth factor receptor inhibition in lung cancer: the evolving role of individualized therapy" Cancer and Metastasis Reviews, pp. 37-48, vol. 29. No. 1 (Feb. 3, 2010).

Rodrigo Dienstmann et al.,"Drug development to overcome resistance to EGFR inhibitors in lung and colorectal cancer", Molecular Oncology, p. 15-26, vol. 6, No. 1(Nov. 25, 2011).

Hua C. Gong et al., "Signatures of Drug Sensitivity in Nonsmall Cell Lung Cancer", International Journal of Proteomics, pp. 1-13, vol. 2011 (Jun. 1, 2011).

H.-J. Nam et al.,"Evaluation of the Antitumor Effects and Mechanisms of PF88299804. a Pan-HER Inhibitor. Alone or in Combination with Chemotherapy or Targeted Agents in Gastric Cancer", Molecular Cancer Therapeutics, pp. 439-451, vol. 11, No. 2(Feb. 1, 2012).

Karen L. Reckamp et al: "A phase 2 trial of dacomitinib (PF-00299884), an oral, irreversible pan-HER (human epidermal growth factor receptor) inhibitor, in patients with advanced non-small cell lung cancer after failure of prior chemotherapy and erlotinib", Cancer, pp. 1145-1154, vol. 120, No. 8 (Apr. 15, 2014).

\* cited by examiner

COMBINATIONS FOR TREATMENT OF CANCER

FIELD OF THE INVENTION

The current disclosure relates to pharmaceutical combinations and compositions useful in the treatment of certain types of cancer. The disclosure also relates to method of treatment of these certain types of cancer. In particular, the disclosure relates to the combined use of inhibitors of MEK, EGFR and ERBB2 in the treatment of KRAS-mutant lung cancer, and KRAS-mutant colon cancer.

PRIOR ART

Cancer is one of the leading causes of death in the Europe and the United States. Despite recent advances in understanding mechanisms involved in cancer and in diagnosis and treatment, drug therapies for metastatic disease are often palliative in nature. Drug therapies seldom offer a long-term cure. There is a constant need for new methods of treatment, either in the form of monotherapy or in the form of combination treatment, combining different new or known drugs as first line therapy, and as second line therapies in treatment of resistant tumors.

Cancer cells are by definition heterogeneous. For example, multiple mutational mechanisms may lead to the development of cancer and mutational mechanisms associated with some cancers may differ between one tissue type and another; it is therefore often difficult to predict whether a specific cancer will respond to a specific chemotherapeutic (Cancer Medicine, 5th edition, Bast et al, B. C. Decker Inc., Hamilton, Ontario).

The treatment of cancer is gradually changing from an organ-centered to a pathway-centered approach. Cancer cells often have an addiction to the signals that are generated by the cancer-causing genes. Consequently, targeted cancer drugs that selectively inhibit the products of activated oncogenes can have dramatic effects on cancer cell viability. This approach has yielded significant clinical results for Non Small Cell Lung Cancer (NSCLC) having activating mutations in EGFR or translocations of the ALK kinase and for melanoma patients having a BRAF mutant tumor. However, this approach has not been successful in all type of cancers, in particular in cancers characterized by oncogenic mutations in one of the members of the RAS gene family, in particular KRAS.

On the other hand, it has been reported that whereas melanoma patients with a specific activating mutation in BRaf(V600E) benefit from treatment with Vemurafenib, an inhibitor that was designed specifically against this mutant form of BRaf, a significant subset of colorectal carcinoma patients having the same mutant fail to respond to treatment with that same drug. The reason why is that in colorectal cancer cells a feedback mechanism is present through which a signaling blockade at the BRaf level can be circumvented. This feedback mechanism is not present in melanoma cells (Prahallad A, et al Nature. 2012 Jan. 26; 483(7387):100-3). This suggests in cancer treatment, pathway information from one type of organ can not directly be transferred to any other organ.

It is a goal of the current invention to provide for new and improved methods of treatment of KRAS-mutant cancer, in particular colon cancer and KRAS-mutant lung cancer, as well as to provide for products and therapeutically pharmaceutical combinations for use in these KRAS-mutant cancers.

DESCRIPTION

Definitions

Figure 1:
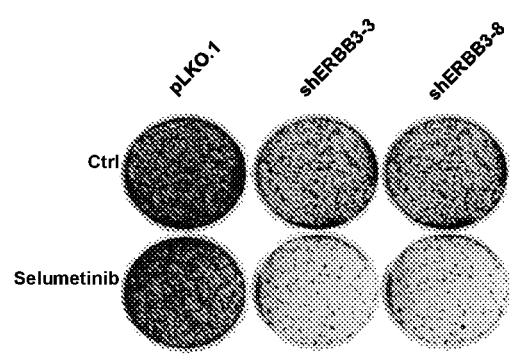
FIG. 1 Suppression of ERBB3 by shRNA enhances response to MEK inhibitor. H358 KRAS mutant (Non-Small Cell Lung Cancer (NSCLC) cells were infected with two independent shRNAs targeting ERBB3 as indicated. pLKO vector serves as a control vector. After puromycin selection, cells were cultured in the absence or presence of 1 µM selumetinib for 20 days.

Unless defined otherwise, technical and scientific terms used herein have the same meaning as commonly understood by one of ordinary skill in the art to which this disclosure belongs. One skilled in the art will recognize many methods and materials similar or equivalent to those described herein, which could be used in the practice of the present invention. Indeed, the present invention is in no way limited to the methods and materials described.

For purposes of the present invention, the following terms are defined below.

As used herein, the singular forms "a," "an" and "the" include plural referents unless the context clearly dictates otherwise. For example, a method for administrating a drug includes the administrating of a plurality of molecules (e.g. 10's, 100's, 1000's, 10's of thousands, 100's of thousands, millions, or more molecules).

As used herein, the term "and/or" indicates that one or more of the stated cases may occur, alone or in combination with at least one of the stated cases, up to with all of the stated cases.

As used herein, with "At least" a particular value means that particular value or more. For example, "at least 2" is understood to be the same as "2 or more" i.e., 2, 3, 4, 5, 6, 7, 8, 9, 10, 11, 12, 13, 14, 15, . . . , etc.

As used herein "cancer" and "cancerous", refer to or describe the physiological condition in mammals that is typically characterized by unregulated cell growth. Examples of cancer include, but are not limited to, colon cancer and lung cancer. Cancer is also referred to as malignant neoplasm.

As used herein, "in combination with" is intended to refer to all forms of administration that provide a first drug together with a further (second, third) drug. The drugs may be administered simultaneous, separate or sequential and in any order. Drugs administered in combination have biological activity in the subject to which the drugs are delivered.

As used herein, "colon cancer", or "colorectal cancer" relates to a cancer from uncontrolled cell growth in the colon or rectum, or in the appendix.

As used herein, "to comprise" and its conjugations is used in its non-limiting sense to mean that items following the word are included, but items not specifically mentioned are not excluded. It also encompasses the more limiting "to consist of".

A used herein "compositions", "products" or "combinations" useful in the methods of the present disclosure include those suitable for various routes of administration, including, but not limited to, intravenous, subcutaneous, intradermal, subdermal, intranodal, intratumoral, intramuscular, intraperitoneal, oral, nasal, topical (including buccal and sublingual), rectal, vaginal, aerosol and/or parenteral or mucosal application. The compositions, formulations, and products according to the disclosure invention normally comprise the drugs (alone or in combination) and one or more suitable pharmaceutically acceptable excipients.

As used herein, "an effective amount" is meant the amount of an agent required to ameliorate the symptoms of a disease relative to an untreated patient. The effective amount of active agent(s) used to practice the present invention for therapeutic treatment of a cancer varies depending upon the manner of administration, the age, body weight, and general health of the subject. Ultimately, the attending physician or veterinarian will decide the appropriate amount and dosage regimen. Such amount is referred to as an "effective" amount. Thus, in connection with the administration of a drug which, in the context of the current disclosure, is "effective against" a disease or condition indicates that administration in a clinically appropriate manner results in a beneficial effect for at least a statistically significant fraction of patients, such as an improvement of symptoms, a cure, a reduction in at least one disease sign or symptom, extension of life, improvement in quality of life, or other effect generally recognized as positive by medical doctors familiar with treating the particular type of disease or condition.

As used herein, "lung cancer" is cancer that accounts for almost one third of cancer deaths, and is broadly classified into two types: non-small-cell lung cancer and small cell lung cancer. Non-small-cell lung cancer (NSCLC) comprises 80-85% of lung cancer cases and different types of NSCLC are named based on the kinds of cells found in the cancer and how the cells look under a microscope. NSCLC comprises squamous cell carcinoma, large cell carcinoma, which begins in several types of large lung cells and adenocarcinoma, which begins in the cells that line the alveoli of the lung and make substances such as mucus. Small cell lung cancer is a form of highly malignant lung cancer that is composed of small ovoid cells. In an embodiment of the invention, the lung cancer is non-small-cell lung cancer; in another embodiment of the invention, the lung cancer is small cell lung cancer.

DETAILED DESCRIPTION

The current disclosure is based on the surprising finding that a combination of inhibitors of the proteins (enzymes) MEK, EGFR and ERBB2 is highly synergetic in inhibiting proliferation of or inducing apoptosis in KRAS-mutant cancers, in particular KRAS-mutant lung cancer cells and in KRAS-mutant colon cancer cells. In addition, the claimed combination works particularly well in those cells that are relatively insensitive to inhibition by MEK-inhibitors alone.

The inventors of the present invention have demonstrated via experiments, that the combination of a MEK-inhibitor, an EGFR-inhibitor and an ERBB2-inhibitor manifests an unexpected and strong synergistic, therapeutic effect on the treatment of KRAS-mutant lung cancer and KRAS-mutant colon cancer. Based on experimental data, the present inventors believe (without being bound by theory) that specifically in KRAS mutant lung cancer and KRAS mutant colon cancer, MEK inhibition leads to the MYC-dependent formation of kinase-active EGFR-ERBB3 and ERBB2-ERBB3 heterodimeric complexes which can be inhibited to enable the colon cancer or lung cancer cells to respond to MEK inhibition.

The combination disclosed herein exhibits therapeutic synergy. Therapeutic synergy may be demonstrated by the showing that the combination is superior to one or other of the constituents used at its optimum dose.

In a first aspect of the disclosure there is provided for an MEK-inhibitor for use in treatment of KRAS-mutant lung cancer or KRAS-mutant colon cancer, wherein the MEK-inhibitor is administrated simultaneously, separately or sequentially with an EGFR-inhibitor and simultaneously, separately or sequentially with an ERBB2-inhibitor. In such embodiment, the MEK-inhibitor is for use in treatment of patients, to which, during the treatment, also an inhibitor of EGFR and an inhibitor of ERBB2 is provided, optionally wherein the inhibitor is both an EGFR-inhibitor and an ERBB2-inhibitor. The skilled person will understand that any one of the MEK-inhibitor, the ERGF-inhibitor and the ERBB2-inhibitor may be administrated to the patient simultaneously, separately or sequentially from the other drugs.

The MEK-inhibitor may be administered to the patients either simultaneously, separately or sequentially with the other drug(s). For example, in practice the product leaflet of the MEK-inhibitor may suggest the simultaneous, separate or sequential use of the MEK-inhibitor with the EGFR-inhibitor and the simultaneously, separately or sequentially use with an ERBB2-inhibitor, or simultaneously, separately or sequentially the EGFR- and ERBB2-inhibitor.

In a second aspect there is provided for an EGFR-inhibitor for use in treatment of KRAS-mutant lung cancer or KRAS-mutant colon cancer, wherein the EGFR-inhibitor is administrated simultaneously, separately or sequentially with an ERBB2-inhibitor and simultaneously, separately or sequentially with a MEK-inhibitor.

The EGFR-inhibitor may be administered to the patients either simultaneously, separately or sequentially with the other drug(s). For example, in practice the product leaflet of the EGFR-inhibitor may suggest the simultaneous, separate or sequential use of the EGFR-inhibitor with the MEK-inhibitor and the simultaneously, separately or sequentially use with the ERBB3-inhibitor, or the MEK- and ERBB2-inhibitor.

In a third aspect there is provided for an ERBB2-inhibitor for use in treatment of KRAS-mutant lung cancer or KRAS-mutant colon cancer, wherein the ERBB2-inhibitor is administrated simultaneously, separately or sequentially with an EGFR-inhibitor and simultaneously, separately or sequentially with a MEK-inhibitor.

The ERBB2-inhibitor may be administered to the patients either simultaneously, separately or sequentially with the other drug(s). For example, in practice the product leaflet of the ERBB2-inhibitor may suggest the simultaneous, separate or sequential use of the ERBB2-inhibitor with the EGFR-inhibitor and the simultaneously, separately or sequentially use with the MEK-inhibitor, or the EGFR- and MEK-inhibitor.

As explained above, the new use of the MEK-inhibitor, or the EGFR-inhibitor or the ERBB2-inhibitor is not limited to combinations administered separately, but also includes the compositions obtained by physical association of the drugs and in either case a synergistic effect may be obtained.

As used herein "simultaneous" administration refers to administration of more than one drug at the same time, but not necessarily via the same route of administration or in the form of one combined formulation. For example, one drug may be provided orally whereas the other drug may be provided intravenously during a patients visit to a hospital. Separate includes the administration of the drugs in separate form and/or at separate moments in time, but again, not necessarily via the same route of administration. Sequentially indicates that the administration of a first drug if followed, immediately or in time, by the administration of the second drug.

The combination of drugs disclosed herein will preferably be administered to the patient in a form that is suitable for administration to the patient and in an dose that is efficacious, for example, in the treatment with the inhibitors of MEK, EGFR and ERBB2.

The current disclosure thus relates, in these aspects, to a combination therapy, wherein during the therapy the patient is treated with drugs that are inhibitors of MEK, EGFR and ERBB2. It will be understood by the skilled person, the treatment may comprise the use of drugs that on their own are able to inhibit MEK, EGFR and ERBB2, or drugs that inhibit one or two of MEK, EGFR and ERBB2. In preferred embodiments disclosed throughout the application, the drug that inhibits EGFR and the drug that inhibits ERBB2 is the same, i.e. has the same active moiety, for example afatinib or dacometinib. In other words, such drug may be a pan-ERBB inhibitor, inhibiting more than one ERBB at the same time, for example inhibiting the tyrosine kinases of both ERBB1 (EGFR), ERBB2 (HER2) and ERBB4. Other examples are dual-ERBB inhibitors, for example inhibiting ERBB1 (EGFR) and ERBB2 (HER2).

The therapy is suitable for use in patients with KRAS-mutant lung cancer, in particular NSCLC, or a KRAS-mutant colon cancer. The term "KRAS-mutant cancer", and therefore KRAS-mutant lung cancer or KRAS-mutant colon cancer, is well known to the skilled person. A comprehensive overview of RAS mutations in cancer was reported by Prior et al (2012) Cancer Res; 2457-67. KRAS-mutant cells promote oncogenesis due to being mutationally activated, in most cases, at codon 12, 13 and 61. In total forty-four separate point mutations have been characterized in RAS isoforms, with 99.2% in codons 12, 13 and 61.

The GTPase KRas also known as V-Ki-ras2 Kirsten rat sarcoma viral oncogene homolog or KRAS, is a protein that in humans is encoded by the KRAS gene. KRAS acts as a molecular on/off switch. Once it is turned on it recruits and activates proteins necessary for the propagation of growth factor and other receptors' signal, such as c-Raff and PI 3-kinase.

The protein product of the normal KRAS gene performs an essential function in normal tissue signaling, and the mutation of a KRAS gene is an essential step in the development of many cancers. Like other members of the Ras family, the KRAS protein is a GTPase and is an early player in many signal transduction pathways.

MEK comprises both MEK1 and MEK2: MAP/ERK kinase 1, MEK1, PRKMK1, MAPKK1, MAP2K1, MKK1 are the same enzyme, known as MEK1, MAP/ERK kinase 2, MEK2, PRKMK2, MAPKK2, MAP2K2, MKK2 are the same enzyme, known as MEK2. MEK1 and MEK2, together MEK, can phosphorylate serine, threonine and tyrosine residues in protein or peptide substrates. To date, few cellular substrates of MEK isoforms have been identified.

Methods to determine MEK-inhibitors (inhibiting MEK 1, MEK2 or both) are known in the art, for example as described in detail in EP2496575.

Examples of drugs that inhibit MEK include sorafenib, PD-0325901 (Pfizer), AZD-8330 (AstraZeneca), RG-7167 (Roche/Chugai), RG-7304 (Roche), CIP-137401 (Cheminpharma), WX-554 (Wilex; UCB), SF-2626 (Semafore Pharmaceuticals Inc), RO-5068760 (F Hoffmann-La Roche AG), RO-4920506 (Roche), G-573 (Genentech) and G-894 (Genentech), N-acyl sulfonamide prodrug GSK-2091976A (GlaxoSmithKline), BI-847325 (Boehringer Ingelheim), WYE-130600 (Wyeth/Pfizer), ERK1-624, ERK1-2067, ERK1-23211, AD-GL0001 (ActinoDrug Pharmaceuticals GmbH), selumetinib (AZD6244), trametinib, TAK-733, Honokiol, MEK-162, derivates, and salts thereof. One or more of the above MEK inhibitors may preferably be used in the compositions, combinations, products and methods according to the current invention, for example sorafenib, PD-0325901, AZD-8330, RG-7167, RG-7304, CIP-137401, WX-554, SF-2626, RO-5068760, RO-4920506, G-573 and G-894, N-acyl sulfonamide prodrug GSK-2091976A, BI-847325, WYE-130600, ERK1-624, ERK1-2067, ERK1-23211, AD-GL0001, selumetinib (AZD6244), trametinib, TAK-733, Honokiol, MEK-162, or derivates or salts thereof.

EGFR, or Epidermal Growth Factor Receptor (EGFR) is a member of the type 1 tyrosine kinase family of growth factor receptors. EGFR plays a critical role in cellular growth, differentiation, and survival. Activation of these receptors typically occurs via specific ligand binding, resulting in hetero- or homodimerization between receptor family members, with subsequent autophosphorylation of the tyrosine kinase domain. This activation triggers a cascade of intracellular signaling pathways involved in both cellular proliferation and survival. Members of this family, including EGFR and HER2, have been directly implicated in cellular transformation.

Methods to determine EGFR-inhibitors are known in the art, for example as described in detail in EP1877398.

Examples of drugs that inhibit EGFR include Tarceva™ (also known as erlotinib; OSI-774). It is a selective inhibitor of EGFR tyrosine kinase. Erlotinib inhibits human EGFR tyrosine kinase with an IC50 of 2 nM (0.786 mg/mL) in an in vitro enzyme assay. Other examples of EGFR inhibitors include erlotinib, panitumumab (Abgenix), vandetanib (AstraZeneca), icotinib (hydrochloride; Beta Pharma), CO-1686 (Avila Therapeutics), AZD-4769, poziotinib (Hanmi Pharmaceutical Co Ltd), CUDC-101 (Curis), Exelixis, S-222611 (Shioogi), AC-480 (Ambit), imgatuzumab (Glycart Biotechnology AG), sapitinib, TAS-2913 (Taiho Pharmaceutical Co Ltd), theliatinib (Hutchison Medipharma Enterprises Ltd), XGFR-2421 (Glycart), HM-61713B (Hanmi Pharmaceutical Co Ltd), epitinib (Hutchison Medipharma Enterprises Ltd), NRC-2694 (Natco), MLBS-42 (ProQinase GmbH), JRP-890 (Prous Institute For Biomedical Research Sa), cetuximab, AL-6802 (Advenchen Laboratories LLC), TAK-285 (Takeda), BGB-102 (Johnson & Johnson), AEE-788 (Novartis), gefitinib, DMS-3008 (Domantis Ltd), TX-2036 (University of Tokushima), KI-6783, KI-6896 (Kirin Brewery Co Ltd), derivates and salts thereof. One or more of the above EGFR-inhibitors may preferably be used in the compositions, combinations, products and methods according to the current invention, for example erlotinib, panitumumab (Abgenix), vandetanib (AstraZeneca), icotinib (hydrochloride; Beta Pharma), CO-1686 (Avila Therapeutics), AZD- 4769, poziotinib (Hanmi Pharmaceutical Co Ltd), CUDC-101 (Curis), Exelixis, S-222611 (Shioogi), AC-480 (Ambit), imgatuzumab (Glycart Biotechnology AG), sapitinib, TAS-2913 (Taiho Pharmaceutical Co Ltd), theliatinib (Hutchison Medipharma Enterprises Ltd), XGFR-2421 (Glycart), HM-61713B (Hanmi Pharmaceutical Co Ltd), epitinib (Hutchison Medipharma Enterprises Ltd), NRC-2694 (Natco), MLBS-42 (ProQinase GmbH), JRP-890 (Prous Institute For Biomedical Research Sa), cetuximab, AL-6802 (Advenchen Laboratories LLC), TAK-285 (Takeda), BGB-102 (Johnson & Johnson), AEE-788 (Novartis), gefitinib, DMS-3008 (Domantis Ltd), TX-2036 (University of Tokushima), KI-6783, KI-6896 (Kirin Brewery Co Ltd), afatinib, dacometinib, derivates or salts thereof.

ERBB2 is a tyrosine kinase receptor that belongs to the ErbB family of receptors, which comprises four closely related members: EGF receptor (EGFR), ErbB2/Neu/HER2, ErbB3 and ErbB4. ErbB receptors are expressed in a variety of tissues of epithelial, mesenchymal and neuronal origin, where they play fundamental roles in development, proliferation, differentiation and angiogenesis. These receptors are activated by numerous ErbB-specific ligands that bind the extracellular domains and lead to the formation of both homo- and heterodimers.

Methods to determine ERBB2-inhibitors are known in the art, for example as described in detail in EP1877398.

Examples of drugs that inhibit ERBB2 include Herceptin, pertuzumab, trastuzumab, dacomitinib, (ERBB2) antibodies as described in WO-2012162561, neratinib, allitinib tosylate, poziotinib, CUDC-101 (Curis), BT-2111 (biOsasis), margetuximab, Exelixis, NT-004 or NT-113 (Jiangsu Kanion Pharmaceutical Co Ltd), S-222611 (Shionogi & Co Ltd), AG879, Mubritinib, AC-480 (Bristol-Myers Squibb Co), sapitinib, MM-111 (Merrimack Pharmaceuticals Inc), PR-610 (University of Auckland), cipatinib trastuzumab-duocarmycin, Prolanta, varlitinib, kahalalide F, TrasGEX, masoprocol, ARRY-380 (Array BioPharma), erbicinumab, HuMax-Her2, CP-724714 (Pfizer), COVA-208 (Covagen), lapatinib and pazopanib, AEE-788 (Novartis), canertinib, pelitinib, BMS-690514 (Bristol-Meyers Squibb), afatinib, dacometinib, derivates and salts thereof. One or more of the above EGFR-inhibitors may preferably be used in the compositions, combinations, products and methods according to the current invention, for example pertuzumab, trastuzumab, dacomitinib, antibodies as described in WO-2012162561, neratinib, allitinib tosylate, poziotinib, CUDC-101 (Curis), BT-2111 (biOsasis), margetuximab, Exelixis, NT-004 or NT-113 (Jiangsu Kanion Pharmaceutical Co Ltd), S-222611 (Shionogi & Co Ltd), AG879, Mubritinib, AC-480 (Bristol-Myers Squibb Co), sapitinib, MM-111 (Merrimack Pharmaceuticals Inc), PR-610 (University of Auckland), cipatinib trastuzumab-duocarmycin, Prolanta, varlitinib, kahalalide F, TrasGEX, masoprocol, ARRY-380 (Array BioPharma), erbicinumab, HuMax-Her2, CP-724714 (Pfizer), COVA-208 (Covagen), lapatinib and pazopanib, AEE-788 (Novartis), canertinib, pelitinib, BMS-690514 (Bristol-Meyers Squibb), afatinib, dacometinib, derivates and salts thereof.

In a preferred embodiment of the above aspects, the EGFR-inhibitor and the ERBB2-inhibitor are the same inhibitor. In this embodiment, the treatment may thus comprise the use of a MEK-inhibitor in combination with a so-called dual-inhibitor of both EGFR and ERBB2. Methods to determine dual inhibitors belong to the knowledge of the person skilled in the art, and for example, as described in EP1877398. Preferred examples of such drug include afatinib or dacometinib.

In another preferred embodiment, the MEK-inhibitor is selected from the group consisting of sorafenib, PD-0325901 (Pfizer), AZD-8330 (AstraZeneca), RG-7167 (Roche/Chugai), RG-7304 (Roche), CIP-137401 (Cheminpharma), WX-554 (Wilex; UCB), SF-2626 (Semafore Pharmaceuticals Inc), RO-5068760 (F Hoffmann-La Roche AG), RO-4920506 (Roche), G-573 (Genentech) and G-894 (Genentech), N-acyl sulfonamide prodrug GSK-2091976A (GlaxoSmithKline), BI-847325 (Boehringer Ingelheim), WYE-130600 (Wyeth/Pfizer), ERK1-624, ERK1-2067, ERK1-23211, AD-GL0001 (ActinoDrug Pharmaceuticals GmbH), selumetinib (AZD6244), trametinib, TAK-733, Honokiol, MEK-162, derivates, and salts thereof.

In another preferred embodiment, the EGFR-inhibitor is selected from the group consisting of erlotinib, panitumumab (Abgenix), vandetanib (AstraZeneca), icotinib (hydrochloride; Beta Pharma), CO-1686 (Avila Therapeutics), AZD-4769, poziotinib (Hanmi Pharmaceutical Co Ltd), CUDC-101 (Curis), Exelixis, S-222611 (Shioogi), AC-480 (Ambit), imgatuzumab (Glycart Biotechnology AG), sapitinib, TAS-2913 (Taiho Pharmaceutical Co Ltd), theliatinib (Hutchison Medipharma Enterprises Ltd), XGFR-2421 (Glycart), HM-61713B (Hanmi Pharmaceutical Co Ltd), epitinib (Hutchison Medipharma Enterprises Ltd), NRC-2694 (Natco), MLBS-42 (ProQinase GmbH), JRP-890 (Prous Institute For Biomedical Research Sa), cetuximab, AL-6802 (Advenchen Laboratories LLC), TAK-285 (Takeda), BGB-102 (Johnson & Johnson), AEE-788 (Novartis), gefitinib, DMS-3008 (Domantis Ltd), TX-2036 (University of Tokushima), KI-6783, KI-6896 (Kirin Brewery Co Ltd), afatinib, dacometinib and derivates and salts thereof.

In another preferred embodiment the ERBB2-inhibitor is selected from the group consisting of pertuzumab, trastuzumab, dacomitinib, (ERBB2) antibodies as described in WO-2012162561, neratinib, allitinib tosylate, poziotinib, CUDC-101 (Curis), BT-2111 (biOsasis), margetuximab, Exelixis, NT-004 or NT-113 (Jiangsu Kanion Pharmaceutical Co Ltd), S-222611 (Shionogi & Co Ltd), AG879, Mubritinib, AC-480 (Bristol-Myers Squibb Co), sapitinib, MM-111 (Merrimack Pharmaceuticals Inc), PR-610 (University of Auckland), cipatinib trastuzumab-duocarmycin, Prolanta, varlitinib, kahalalide F, TrasGEX, masoprocol, ARRY-380 (Array BioPharma), erbicinumab, HuMax-Her2, CP-724714 (Pfizer), COVA-208 (Covagen), lapatinib and pazopanib, AEE-788 (Novartis), canertinib, pelitinib, BMS-690514 (Bristol-Meyers Squibb), afatinib, dacometinib, derivates and salts thereof.

In another preferred embodiment, the MEK-inhibitor is selumetinib or PD-0325901 (N-[(2R)-2,3-Dihydroxypropoxy]-3,4-difluoro-2-[(2-fluoro-4-iodophenyl)amino]-benzamide), and the EGFR-inhibitor and the ERBB2-inhibitor is afatinib or dacometinib. More preferably, the MEK-inhibitor is PD-0325901, and the EGFR-inhibitor and the ERBB2-inhibitor is dacometinib.

According to another aspect of the current invention, there is provided for product comprising a MEK-inhibitor, an EGFR-inhibitor and an ERBB2-inhibitor as a combined preparation for simultaneous, separate or sequential use in treatment of KRAS-mutant lung cancer or KRAS-mutant colon cancer. As witnessed in the Examples below, the combination of such MEK-inhibitor, EGFR-inhibitor and ERBB2 inhibitor surprisingly synergistically inhibit proliferation and/or induce apoptosis of KRAS-mutant colon cancer cells or KRAS-mutant lung cancer cells.

As detailed above, the product is for simultaneous, separate or sequential use and may comprise the same combination of MEK-inhibitor, EGFR-inhibitor and/or ERBB2-inhibitor as disclosed in the paragraphs above.

According to another aspect of the current invention, there is provided for a therapeutic pharmaceutical product comprising a MEK-inhibitor, an EGFR-inhibitor and an ERBB2-inhibitor. Preferably, the combined preparation is for simultaneous, separate or sequential use in treatment of KRAS-mutant lung cancer or KRAS-mutant colon cancer, as detailed herein. As detailed above, also the combination may comprise the same combination of MEK-inhibitor, EGFR-inhibitor and/or ERBB2-inhibitor as disclosed in the paragraphs above.

In another aspect there is provided for the use of a MEK-inhibitor, an EGFR-inhibitor and/or an ERBB2-inhibitor in the manufacture of a medicament for the treatment of KRAS-mutant lung cancer or KRAS-mutant colon cancer, wherein the treatment comprises the simultaneous, separate or sequential administration of a MEK-inhibitor, EGFR-inhibitor and ERBB2-inhibitor. As detailed above, also the combination may comprise the same combination of MEK-inhibitor, EGFR-inhibitor and/or ERBB2-inhibitor as disclosed in the paragraphs above.

In a last aspect, there is provided for a method for the treatment of KRAS-mutant lung cancer or KRAS-mutant colon cancer, wherein the method comprises simultaneous, separate or sequential administering, in a patient in need thereof, of a MEK-inhibitor, an EGFR-inhibitor and an ERBB2-inhibitor. As detailed above, also the combination may comprise the same combination of MEK-inhibitor, EGFR-inhibitor and/or ERBB2-inhibitor as disclosed in the paragraphs above.

The treatment of the patient includes treatment in the first line or second line, or third line. In particular the disclosure herein can advantageously be used in patients that, e.g. in monotherapy, show reduced response to the use of an MEK-inhibitor, either from the start, or after a certain period of treatment with the MEK-inhibitor, for example patients that are resistant to the MEK-inhibitor.

In a preferred embodiment, the KRAS-mutant cancer is characterized by the expression or increased expression of ERBB3 (or HER3), a receptor tyrosine-protein kinase encoded by the ERBB3 gene.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

EXAMPLES

Example 1

Introduction
Experimental Procedures
Synthetic Lethality shRNA Screen
A kinome-centered shRNA library targeting 535 human kinases and kinase-related genes was assembled from The RNAi Consortium (TRC) human genome-wide shRNA collection (TRC-Hs1.0). The kinome shRNA library was introduced to H358 lung cells by lentiviral transduction. Cells stably expressing shRNA were cultured in the presence or absence of selumetinib. The abundance of each shRNA in the pooled samples is determined by Illumina deep sequencing. shRNAs prioritized for further analysis were selected by the fold depletion of abundance in selumetinib (a MEK inhibitor) treated sample compared with that in untreated sample. Further details are described in (Prahallad et al., 2012).

Tumor Xenograft Experiments

All experiments with mice were performed according to Italian and European guidelines for animal experimentation. Cells (5 million/mouse) were injected subcutaneously in the right posterior flank of 7-week old female nude mice and grown as tumor xenografts. Tumor volume based on caliper measurements was calculated by the modified ellipsoidal formula (tumor volume=1/2(length×width2)). Treatment with afatinib (a dual ERBB2/EGFR inhibitor, 12.5 mg/Kg), trametinib (a MEK inhibitor, 1 mg/kg) or their combination (at the same dose as monotherapy) was started when tumor volume reached approximately 250-300 mm3.

KRAS Mutant NSCLC Patient Samples

Permission was granted by the VUMC medical ethical committee to take biopsies from a KRAS mutant NSCLC patient before and after trametinib treatment for 7 days.

Results

KRAS Mutant Lung and KRAS Mutant Colon Cancer Cell Lines are Unresponsive to MEK Inhibitors To study how KRAS mutant cancer cells respond in vitro to MEK inhibition, we determined the efficacy of the MEK inhibitor selumetinib (AZD6244) in 4 NSCLC (lung) and 4 colon cancer cell lines by long-term proliferation assay. The data shows that all but one colon cancer cell line were relatively insensitive to selumetinib. Consistent with this, of the KRAS mutant cancer cell lines present in the Sanger and CCLE cell line encyclopedias (Barretina et al., 2012; Garnett et al., 2012), the vast majority has an IC50 for selumetinib of over 1 µM. Together, these data from cell lines recapitulate the preclinical animal studies and the early phase clinical trial data that show only a modest activity of MEK inhibition in KRAS mutant tumors (Adjei et al., 2008; Janne et al., 2013; Migliardi et al., 2012).

A Synthetic Lethal Screen with MEK Inhibitor.

Recently the use of a kinome-centered synthetic lethal screening approach, which enables the identification of kinases whose inhibition is strongly synergistic with a cancer drug of interest has been described (Prahallad et al., 2012). In brief, in such a genetic screen a collection of 3530 shRNA vectors that collectively target all 518 human kinases for suppression through RNA interference is introduced into cancer cells through lentiviral infection. Each of these knockdown vectors has a unique DNA-based molecular bar code identifier, which allows quantification of the relative abundance of each of the shRNA vectors in the presence and absence of drug (Prahallad et al., 2012). To find kinases whose suppression synergizes with the MEK-inhibitor selumetinb in KRAS mutant NSCLC (non-small cell lung cancer), we infected selumetinib-resistant H358 lung cells with the kinome shRNA library and cultured cells both in the presence and absence of selumetinib. After 21 days, genomic DNA was isolated from both cells of the treated and untreated populations and the bar codes contained in the shRNA cassettes were recovered by PCR and their abundance determined by deep sequencing. For hit selection, only shRNAs were included for which total mean read frequencies were over 1,000. To minimize the chance in identifying off-target effects, hits were selected based on the presence of at least two individual shRNAs targeting the same gene in the top list. Two independent shRNA vectors targeting the EGFR-related kinase ERBB3 were among the top depleted shRNA vectors on this list. To validate this finding, we infected H358 lung cells with these two ERBB3 shRNA vectors (both of which reduced ERBB3 levels) and cultured these cells with or without the MEK-inhibitor selumetinib for 21 days. Inhibition of ERBB3 did not significantly affect proliferation of H358 lung cells, but suppression of ERBB3 in combination with the MEK-inhibitor selumetinib caused a marked inhibition of proliferation in H358 lung cells (FIG. 1). Similar results were obtained in KRAS mutant SW480 colon cancer cells and H2030 NSCLC lung cells.

Dual EGFR/ERBB2 Inhibitors Synergize with MEK Inhibitors

Figure 2:
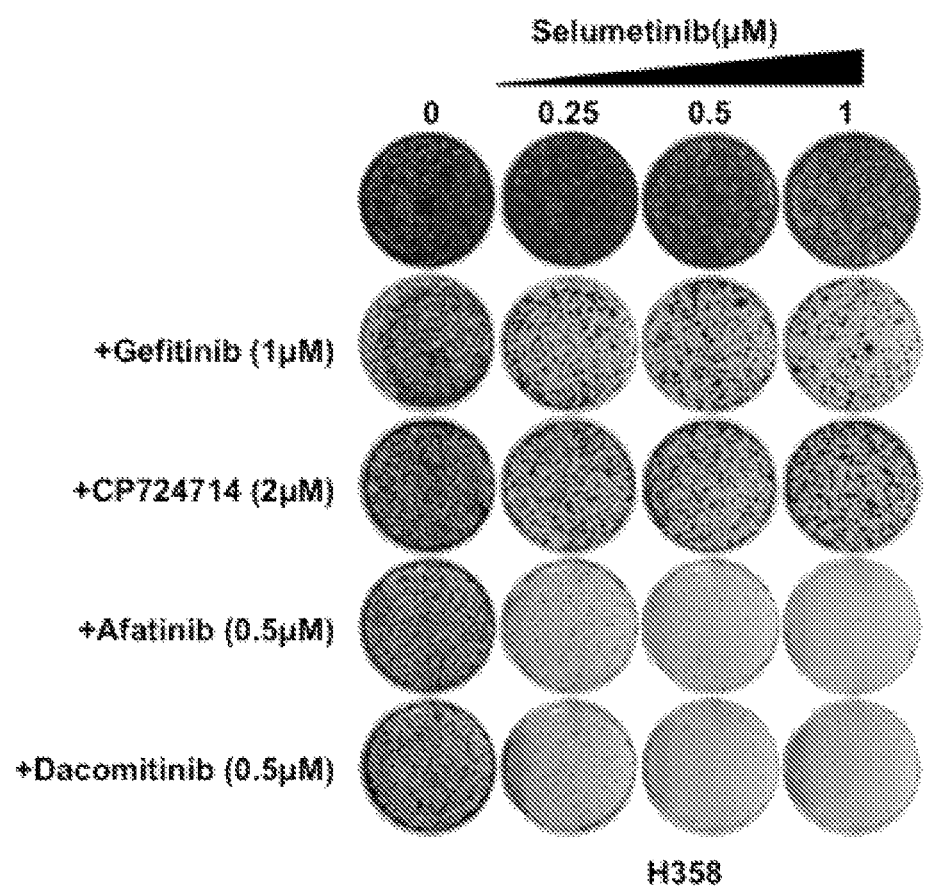
FIG. 2 H538 lung cancer cells were cultured in increasing concentration of MEK inhibitor selumetinib alone, EGFR inhibitor gefitinib alone, ERBB2 inhibitor CP724714 alone, EGFR/ERBB2 dual inhibitor afatinib, EGFR/ERBB2 dual inhibitor dacomitinib alone or their combinations as indicated. Cells were harvested, fixed and stained after 21 days.
Figure 3:
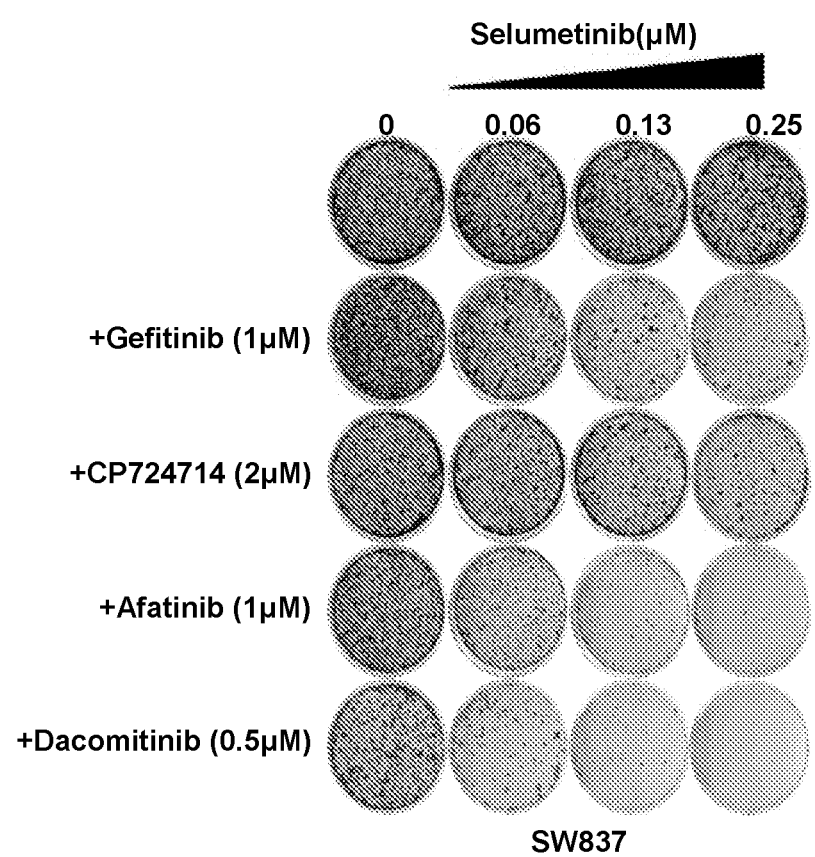
FIG. 3 SW837 colorectal cancer. CRC) cells were cultured in increasing concentration of MEK inhibitor selumetinib alone, EGFR inhibitor gefitinib alone, ERBB2 inhibitor CP724714 alone, EGFR/ERBB2 dual inhibitor afatinib, EGFR/ERBB2 dual inhibitor dacomitinib alone or their combinations as indicated.

ERBB3 is the only kinase-defective member of the ERBB RTK gene family that consists of four members: ERBB1-4. ERBB3 however can form heterodimeric active kinase complexes with other members of the ERBB family that do harbor tyrosine kinase activity (Sithanandam and Anderson, 2008). We found that MEK-inhibitor selumetinib treatment of H358 lung cells caused a marked increase in both ERBB3 and ERBB2 protein. Similar results were obtained in SW837 colon cancer cells and H2030 NSCLC lung cells, suggesting that this is a common response to MEK inhibition in KRAS mutant lung, and KRAS mutant colon cancer. This resulted in an increase in EGFR-ERBB3 and ERBB2-ERBB3 heterodimeric complexes, as judged by co-immunoprecipitation. To ask which of these two heterodimeric complexes could be responsible for the poor response to the MEK inhibitor selumetinib, we treated both H358 lung cells and SW837 colon cells with a combination of selumetinib and the EGFR-inhibitor gefitinib or the combination of the MEK-inhibitor selumetinib and the ERBB2 inhibitor CP724714. Neither of these two combinations showed strong synergy in long-term proliferation assays, but the dual EGFR-ERBB2 inhibitors afatinib and dacometinib each showed strong synergy with MEK inhibition, both in the H358 lung cells and in SW837 colon cells (FIGS. 2 and 3). Similar results were seen in three additional KRAS mutant cells lines: SW620 (colon), H2030 (lung) and H2122 (lung). Moreover, a second MEK inhibitor (GSK1120212, trametinib) also showed strong synergy with the dual EGFR/ERBB2 inhibitor afatinib in four different KRAS mutant colon and lung cancer cell lines. We conclude that MEK inhibition leads to the formation of kinase-active EGFR-ERBB3 and ERBB2-ERBB3 heterodimeric complexes and that both need to be inhibited to enable the colon cancer and lung cancer cells to respond to MEK inhibition. This conclusion is further supported by the notion that only the combination of shRNA vectors against both EGFR and ERBB2 synergize with the MEK inhibitor selumetinib, but not either shRNA vector alone.

MEK Inhibition Causes a MYC-Dependent Transcriptional Upregulation of ERBB3.

The MEK inhibitor selumetinib caused an increase in both total ERBB3 and active phospho-ERBB3 (p-ERBB3) in both H358 lung and in SW837 colon cells and similar effects were seen for ERBB2. MEK-ERK signaling is known to enhance stability of MYC through phosphorylation of the Serine 62 residue (Sears et al., 1999; Sears et al., 2000). Moreover, MYC has been shown to be a negative regulator of ERBB2 transcription (Suen and Hung, 1991). Inhibition of MEK by selumetinib caused a decrease in MYC protein in both NSCLC lung cells and colon cancer cells and this was accompanied by an increase in both ERBB2 and ERBB3 mRNA expression in multiple KRAS mutant cell lines of lung and colon. In addition, knockdown of MYC by two independent shRNAs caused a reduction in MYC protein and an increase in both ERBB2 and ERBB3 mRNA and protein.

Consistent with a role for MYC SER62 phosphorylation in induction of ERBB2 and ERBB3, we found that expression of the phospho-mimetic mutant MYC (SER62D) (Wang et al., 2010) effectively blocked induction of both ERBB2 and ERBB3 by the MEK inhibitor selumetinib. Induction of ERBB2 and ERBB3 was also seen in half of 19 independent patient-derived xenografts from KRAS mutant colorectal cancers that proved to be poorly responsive to selumetinib in vivo (Migliardi et al., 2012). Finally, we were able to obtain a paired biopsy from a patient having a KRAS mutated adenocarcinoma of the lung before and after one week of treatment with the MEK inhibitor trametinib in the context of a randomized phase II clinical trial. Here too, we observed induction of both ERBB2 and ERBB3 by MEK inhibitor treatment, suggesting that this transcriptional RTK activation is potentially also limiting responses to MEK inhibition in the clinic.

Synergistic Inhibition of ERK Causes Apoptosis Through Decreased BAD Phosphorylation.

To address the mechanism by which the MEK inhibitor selumetinib and the dual ERBB2/EGFR inhibitor afatinib synergize to reduce viability of KRAS mutant lung and KRAS mutant colon cancer cells, we assayed induction of apoptosis over a 4-day period in real time in the presence of selumetinib, afatinib or the combination of both drugs. Both the H358 lung and SW837 colon cells displayed only modest evidence of apoptosis following drug monotherapy, but strongly synergistic induction of apoptosis when selumetinib and afatinib were combined. Consistently, both drugs were also highly synergistic in induction of cleaved PARP, a hallmark of apoptotic cells.

The RAF-MEK-ERK signaling cascade inhibits apoptosis in part through induction of pro-apoptotic factors BAD and BIM (Zha et al., 1996) (Corcoran et al., 2013). MEK-ERK inhibition induces BIM and decreases inhibitory phosphorylation of the BAD, which can heterodimerize with BCL-XL and BCL-2, neutralizing their protective effect and promoting cell death. Only the non-phosphorylated BAD forms heterodimers that promote cell death (Zha et al., 1996). BAD can be phosphorylated both by the PI3K-AKT and the MEK-ERK signaling routes on SER112 and SER136, respectively (Bonni et al., 1999; Datta et al., 1997; Scheid et al., 1999). Consistent with the finding that the dual EGFR/ERBB2 inhibitor afatinib and the MEK inhibitor selumetinib synergize to inhibit AKT and ERK signaling, we also observed a clear synergistic inhibition of p-BAD SER112 by these two drugs and suppressed BAD SER136 phosphorylation by adding afatinib. In addition, we see induction of BIM by MEK inhibition and decreased p-BIM SER69 upon ERK inhibition. Finally, we tested whether both drugs acted synergistically to inhibit the growth of KRAS mutant NSCLC lung cells in a mouse xenograft experiment. We observed a modest inhibition of tumor growth by MEK inhibitor alone and the dual EGFR-ERBB2 inhibitor afatinib and a complete inhibition of tumor growth over prolonged time when the two drugs were given together. Together, our data suggest a novel combination therapy for the treatment of KRAS mutant lung cancers, and KRAS mutant colon cancer.

Discussion

We describe here the use of a kinome-centered synthetic lethality screen to identify potential kinases whose inhibition is synergistic with MEK inhibition for the treatment of KRAS mutant lung, e.g. NSCLC and KRAS mutant colon cancers. Our data identify the Receptor Tyrosine Kinase family member ERBB3 as a prominent "hit" in this genetic screen with the MEK inhibitor selumetinib. ERBB3 is not an active kinase itself, but forms active heterodimeric complexes with one of the three other members of the gene family: ERBB1 (EGFR), ERBB2 (HER2) and ERBB4 (which is primarily expressed in the brain). Our data indicate that MEK inhibition in KRAS mutant cancer cells of lung and colon leads to degradation of MYC, consistent with the established role for MEK-ERK signaling in stabilizing MYC through phosphorylation of MYC Serine 62 (Sears et al., 1999; Sears et al., 2000). MYC is also known to act as a transcriptional repressor of ERBB2 (Suen and Hung, 1991). We find here that suppression of MYC not only activates ERBB2, but also ERBB3, indicating that MYC also acts as a repressor of ERBB3. Consequently MEK inhibition causes a transcriptional upregulation of both ERBB2 and ERBB3 and the formation of kinase-active ERBB1-ERBB3 and ERBB2-ERBB3 heterodimeric complexes that activate downstream PI3K-AKT and MEK-ERK signaling. We found that inhibition of EGFR or ERBB2 alone with small molecule drugs did not synergize with MEK inhibition, whereas dual inhibitors of EGFR and ERBB2, such as afatinib and dacometinib, did show strong synergy with MEK inhibition. This explains why only the common dimerization partner of these two active complexes was identified in the synthetic lethality screen.

Due to increased signaling from the active ERBB3 kinase complexes, MEK inhibitors only caused a partial suppression of MEK-ERK signaling in KRAS mutant lung or colon tumors, whereas AKT signaling was even increased in the presence of MEK inhibitors. In contrast, in the presence of both the MEK inhibitor selumetinib and the dual EGFR/ERBB2 inhibitor afatinib, MEK-ERK signaling was more completely inhibited and AKT signaling was also suppressed strongly. We observed a highly synergistic induction of apoptosis when afatinib and selumetinib were combined in KRAS mutant colon and KRAS mutant lung cancer cells. We provide a possible mechanistic explanation for this by showing that the combination of afatinib and selumetinib leads to a more complete inhibition of the phosphorylation of two key inhibitory residues on the pro-apoptotic BH3-only protein BAD and BIM. It has been shown previously that phosphorylation of BAD at Serine residues 112 and 136 sequesters BAD in 14-3-3 protein complexes at the plasma membrane, thereby inhibiting its pro-apoptotic action and a similar model of inhibition by phosphorylation has been proposed for BIM (Datta et al., 1997; Harada et al., 2004; Scheid et al., 1999; Zha et al., 1996). Our data suggest a model in which selumetinib and afatinib synergize to unleash the pro-apoptotic activity of BAD and BIM, resulting in cell death.

Our data identify the release of BH3-only proteins as key events in induction of cell death in conjunction with MEK inhibition. In theory, the use of upstream inhibitors like afatinib that shut down the MEK-ERK and PI3K-AKT pathways should be more effective than a more downstream inhibition of the apoptotic effector proteins. Indeed, Corcoran witnessed in their xenograft model that most residual tumors showed a partial recovery of P-ERK, indicating that failure to maintain full MAPK pathway suppression may contribute to the development of resistance to the selumetinib plus ABT-263 combination (Corcoran et al., 2013). However, clinical success is not only determined by how well the target is inhibited, but also by how well the patients tolerate a particular drug combination.

Summary

There are currently no effective targeted therapies for the some 30% of all human malignancies that have mutations in RAS oncogenes. Using a kinome-centered synthetic lethality screen we find that suppression of the ERBB3 Receptor Tyrosine kinase is strongly synergistic with MEK inhibitors in KRAS mutant lung cancer cells, and KRAS mutant colon cancer cells. We show that MEK inhibition results in MYC-dependent transcriptional upregulation of ERBB3, which is responsible for drug resistance. Small molecule inhibitors targeting both EGFR and ERBB2, each capable of forming active heterodimers with ERBB3, can reverse this intrinsic resistance by decreasing inhibitory phosphorylation of the pro-apoptotic BH3-only proteins BAD and BIM and induction of apoptosis. These data suggest a combination strategy to treat KRAS mutant lung cancers, and KRAS mutant colon cancers.

Oncogenic mutations in RAS genes are frequent in human malignancies, but effective RAS inhibitors have yet to be identified. Drugs that inhibit the RAS downstream kinases RAF, MEK and ERK have been developed, providing a possible strategy to treat RAS mutant tumors. However, preclinical and clinical studies indicate that KRAS mutant lung cancers and KRAS mutant colon carcinomas manifest intrinsic resistance to inhibitors of the MEK kinases. We have used a synthetic lethality genetic screen to find kinases whose suppression is strongly synergistic with MEK inhibition in KRAS mutant lung cancers and KRAS mutant colon cancers. Our data identify a powerful combination therapy for the treatment of both KRAS mutant lung cancer, and KRAS mutant colon cancer.

REFERENCES

Adjei, A. A., Cohen, R. B., Franklin, W., Morris, C., Wilson, D., Molina, J. R., Hanson, L. J., Gore, L., Chow, L., Leong, S., et al. (2008). Phase I pharmacokinetic and pharmacodynamic study of the oral, small-molecule mitogen-activated protein kinase kinase 1/2 inhibitor AZD6244 (ARRY-142886) in patients with advanced cancers. J Clin Oncol 26, 2139-2146.

Barretina, J., Caponigro, G., Stransky, N., Venkatesan, K., Margolin, A. A., Kim, S., Wilson, C. J., Lehar, J., Kryukov, G. V., Sonkin, D., et al. (2012). The Cancer Cell Line Encyclopedia enables predictive modelling of anticancer drug sensitivity. Nature 483, 603-607.

Bernards, R. (2012). A missing link in genotype-directed cancer therapy. Cell 151, 465-468.

Bonni, A., Brunet, A., West, A. E., Datta, S. R., Takasu, M. A., and Greenberg, M. E. (1999). Cell survival promoted by the Ras-MAPK signaling pathway by transcription-dependent and -independent mechanisms. Science 286, 1358-1362.

Bos, J. L. (1989). ras oncogenes in human cancer: a review [published erratum appears in Cancer Res 1990 Feb. 15; 50(4):1352]. [Review]. Cancer Res 49, 4682-4689.

Corcoran, R. B., Cheng, K. A., Hata, A. N., Faber, A. C., Ebi, H., Coffee, E. M., Greninger, P., Brown, R. D., Godfrey, J. T., Cohoon, T. J., et al. (2013). Synthetic Lethal Interaction of Combined BCL-XL and MEK Inhibition Promotes Tumor Regressions in KRAS Mutant Cancer Models. Cancer Cell 23, 121-128.

Datta, S. R., Dudek, H., Tao, X., Masters, S., Fu, H., Gotoh, Y., and Greenberg, M. E. (1997). Akt phosphorylation of BAD couples survival signals to the cell-intrinsic death machinery. Cell 91, 231-241.

Flaherty, K. T., Infante, J. R., Daud, A., Gonzalez, R., Kefford, R. F., Sosman, J., Hamid, O., Schuchter, L., Cebon, J., Ibrahim, N., et al. (2012). Combined BRAF and MEK inhibition in melanoma with BRAF V600 mutations. N Engl J Med 367, 1694-1703.

Flaherty, K. T., Puzanov, I., Kim, K. B., Ribas, A., McArthur, G. A., Sosman, J. A., O'Dwyer, P. J., Lee, R. J., Grippo, J. F., Nolop, K., et al. (2010). Inhibition of mutated, activated BRAF in metastatic melanoma. N Engl J Med 363, 809-819.

Garnett, M. J., Edelman, E. J., Heidorn, S. J., Greenman, C. D., Dastur, A., Lau, K. W., Greninger, P., Thompson, I. R., Luo, X., Soares, J., et al. (2012). Systematic identification of genomic markers of drug sensitivity in cancer cells. Nature 483, 570-575.

Harada, H., Quearry, B., Ruiz-Vela, A., and Korsmeyer, S. J. (2004). Survival factor-induced extracellular signal-regulated kinase phosphorylates BIM, inhibiting its association with BAX and proapoptotic activity. Proc Natl Acad Sci USA 101, 15313-15317.

Janne, P. A., Shaw, A. T., Pereira, J. R., Jeannin, G., Vansteenkiste, J., Barrios, C., Franke, F. A., Grinsted, L., Zazulina, V., Smith, P., et al. (2013). Selumetinib plus docetaxel for KRAS-mutant advanced non-small-cell lung cancer: a randomised, multicentre, placebo-controlled, phase 2 study. Lancet Oncol 14, 38-47.

Kwak, E. L., Bang, Y. J., Camidge, D. R., Shaw, A. T., Solomon, B., Maki, R. G., Ou, S. H., Dezube, B. J., Janne, P. A., Costa, D. B., et al. (2010). Anaplastic lymphoma kinase inhibition in non-small-cell lung cancer. N Engl J Med 363, 1693-1703.

Lynch, T. J., Bell, D. W., Sordella, R., Gurubhagavatula, S., Okimoto, R. A., Brannigan, B. W., Harris, P. L., Haserlat, S. M., Supko, J. G., Haluska, F. G., et al. (2004). Activating mutations in the epidermal growth factor receptor underlying responsiveness of non-small-cell lung cancer to gefitinib. N Engl J Med 350, 2129-2139.

Migliardi, G., Sassi, F., Torti, D., Galimi, F., Zanella, E. R., Buscarino, M., Ribero, D., Muratore, A., Massucco, P., Pisacane, A., et al. (2012). Inhibition of MEK and PI3K/mTOR suppresses tumor growth but does not cause tumor regression in patient-derived xenografts of RAS-mutant colorectal carcinomas. Clin Cancer Res 18, 2515-2525.

Montero-Conde, C., Ruiz-Llorente, S., Dominguez, J. M., Knauf, J. A., Viale, A., Sherman, E. J., Ryder, M., Ghossein, R. A., Rosen, N., and Fagin, J. A. (2013). Relief of feedback inhibition of HER3 transcription by RAF and MEK inhibitors attenuates their antitumor effects in BRAF mutant thyroid carcinomas. Cancer Discov.

Prahallad, A., Sun, C., Huang, S., Di Nicolantonio, F., Salazar, R., Zecchin, D., Beijersbergen, R. L., Bardelli, A., and Bernards, R. (2012). Unresponsiveness of colon cancer to BRAF(V600E) inhibition through feedback activation of EGFR. Nature 483, 100-103.

Pylayeva-Gupta, Y., Grabocka, E., and Bar-Sagi, D. (2011). RAS oncogenes: weaving a tumorigenic web. Nature reviews 11, 761-774.

Scheid, M. P., Schubert, K. M., and Duronio, V. (1999). Regulation of bad phosphorylation and association with Bcl-x(L) by the MAPK/Erk kinase. J Biol Chem 274, 31108-31113.

Sears, R., Leone, G., DeGregori, J., and Nevins, J. R. (1999). Ras enhances Myc protein stability. Mol Cell 3, 169-179.

Sears, R., Nuckolls, F., Haura, E., Taya, Y., Tamai, K., and Nevins, J. R. (2000). Multiple ras-dependent phosphorylation pathways regulate myc protein stability. Genes Dev 14, 2501-2514.

Sithanandam, G., and Anderson, L. M. (2008). The ERBB3 receptor in cancer and cancer gene therapy. Cancer gene therapy 15, 413-448.

Suen, T. C., and Hung, M. C. (1991). c-myc reverses neu-induced transformed morphology by transcriptional repression. Mol Cell Biol 11, 354-362.

Wang, J., Kim, J., Roh, M., Franco, O. E., Hayward, S. W., Wills, M. L., and Abdulkadir, S. A. (2010). Pim1 kinase synergizes with c-MYC to induce advanced prostate carcinoma. Oncogene 29, 2477-2487.

Weinstein, I. B. (2002). Cancer. Addiction to oncogenes—the Achilles heal of cancer. Science 297, 63-64.

Zha, J., Harada, H., Yang, E., Jockel, J., and Korsmeyer, S. J. (1996). Serine phosphorylation of death agonist BAD in response to survival factor results in binding to 14-3-3 not BCL-X(L). Cell 87, 619-628.

The invention claimed is:

1. A method for the treatment of KRAS-mutant lung cancer, or KRAS-mutant colon cancer, wherein the method comprises administering to a patient in need thereof a combination of synergistically effective amounts of a MEK-inhibitor and a dual EGFR/ERBB2 inhibitor, wherein the combination is administered simultaneously as a single combined formulation or as separate formulations, or administered separately but substantially immediately in sequence.

2. The method according to claim 1, wherein the MEK-inhibitor is PD-0325901, and the dual EGFR/ERBB2 inhibitor is dacomitinib.

3. The method according to claim 1, wherein the MEK-inhibitor is Selumetinib and the dual EGFR/ERBB2 inhibitor is Dacomitinib.

4. The method according to claim 1, wherein the MEK-inhibitor is Selumetinib and the dual EGFR/ERBB2 inhibitor is Afatinib.

5. The method according to claim 1, wherein the MEK-inhibitor is Trametinib and the dual EGFR/ERBB2 inhibitor is Afatinib.

* * * * *